US005523229A

United States Patent [19]

Feinberg et al.

[11] Patent Number: 5,523,229
[45] Date of Patent: Jun. 4, 1996

[54] ANTIBODIES SPECIFIC FOR ONCOFETAL FIBRONECTIN

[75] Inventors: Ronald F. Feinberg, Cherry Hill, N.J.; Harvey J. Kliman, Woodbridge, Conn.

[73] Assignee: Trustees of the University of Pennsylvania, Philadelphia, Pa.

[21] Appl. No.: 215,906

[22] Filed: Mar. 22, 1994

[51] Int. Cl.$^6$ ............................. C12N 5/12; C07K 16/18; C07K 14/78; G01N 33/53

[52] U.S. Cl. ............... 435/240.27; 435/7.2; 530/388.25; 530/387.1; 530/388.1; 530/380

[58] Field of Search ........................... 530/387.7, 388.25, 530/387.1, 388.1, 380; 435/240.27, 7.2

[56] References Cited

U.S. PATENT DOCUMENTS 4,894,326  1/1990  Matsuura et al. ........................ 435/7

OTHER PUBLICATIONS

Matsuura et al., "The Oncofetal Structure of Human Fibronectin Defined by Monoclonal Antibody FDC–6", *J. Biol. Chem.* 263: 3314–3322 (1988).

Matsuura et al., "An α–N–Acetylgalactosaminylation at the Threonine Residue of a Defined Peptide Sequence Creates the Oncofetal Peptide Epitope in Human Fibronectin", *J. Biol. Chem.* 264: 10472–10476 (1989).

Matsuura and Hakomori, "The Oncofetal Domain of Fibronectin Defined by Monoclonal Antibody FDC–6: Its Presence in Fibronectins from Fetal and Tumor Tissues and Its Absence in those from Normal Adult Tissues and Plasma", *Proc. Natl. Acad. Sci. USA* 82: 6517–6521 (1985).

Mandel, V. et al, APMIS, 100(9):817–826, 1992.

Loridon–Rosa, B. et al., Cancer Res., 50(5):1608–1612, 1990.

*Primary Examiner*—Lila Feisse
*Assistant Examiner*—Susan A. Loring
*Attorney, Agent, or Firm*—Woodcock Washburn Kurtz Mackiewicz & Norris

[57] ABSTRACT

Immunologic binding partners which specifically bind to oncofetal fibronectin but not normal adult fibronectin or blood plasma fibronectin and methods of diagnosing and treating oncogenesis and reproductive abnormalities employing the same.

6 Claims, 7 Drawing Sheets

X18A4

X15H1 a b c d e f  g h i

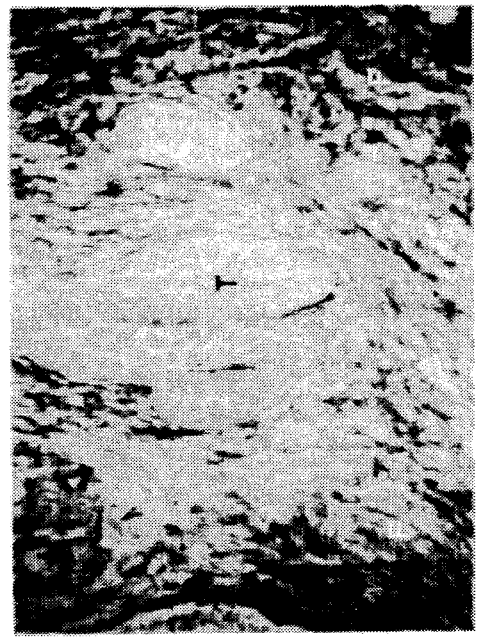

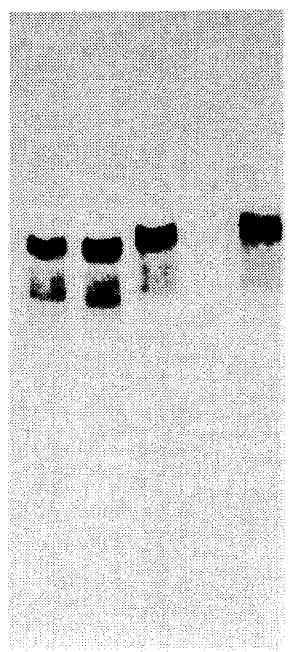 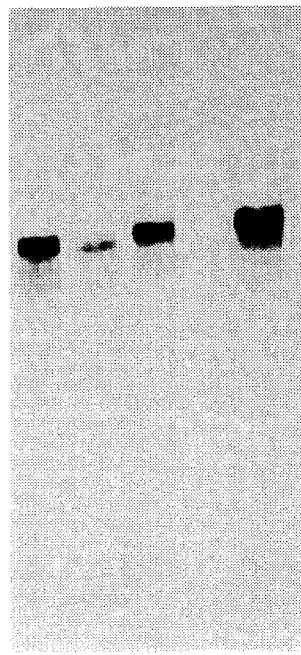 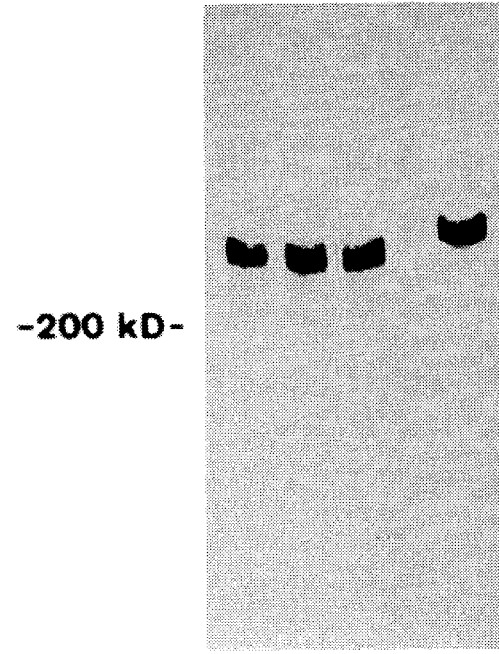
−200 kD−
a b c d    e f g h    i j k l
FIG.6A    FIG.6B    FIG.6C
FIG.7A <sup>FDC-6</sup> 
−200 kD
FIG.7B <sup>X18A4</sup> 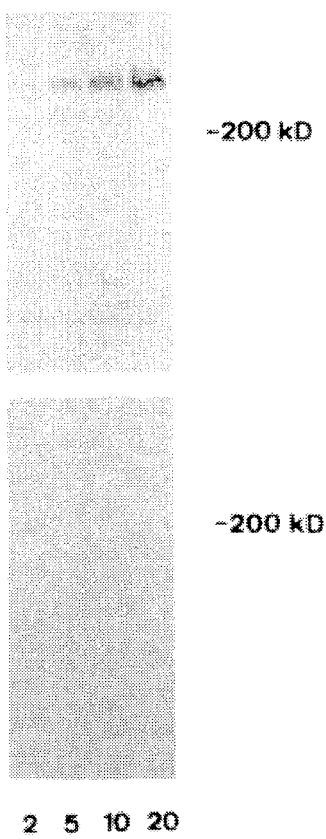
−200 kD
2 5 10 20

ANTIBODIES SPECIFIC FOR ONCOFETAL FIBRONECTIN

FIELD OF THE INVENTION

This invention relates to novel antibodies which specifically bind to oncofetal fibronectin, a fibronectin which has been found to be important in female fertility and involved in human oncogenesis.

BACKGROUND OF THE INVENTION

Oncofetal fibronectin, a distinct class of adhesive extracellular matrix (ECM) molecules, has recently been associated with the biological processes of trophoblastic implantation, placentation, and chorionic membrane stability (Feinberg et al., *Am J of Pathology* 138:537–543 (1991); Feinberg and Kliman, *Troph Res* 7:167–179 (1993); Cunningham et al., eds. *Williams Obstetrics 19th Edition.* Norwalk, Conn.: Appleton and Lange, 122 (1993)). During pregnancy, oncofetal fibronectin is normally found within the trophoblast-associated ECM of the uteroplacental junction and chorion, (Feinberg et al., *Am J of Pathology* 138: 537–543 (1991); Feinberg and Kliman, *Troph Res* 7:167–179 (1993); Cunningham et al., eds. *Williams Obstetrics 19th Edition.* Norwalk, Conn.: Appleton and Lange, 122 (1993)) as well as in soluble form in amniotic fluid (Matsuura and Hakomori *Proc Natl Acad Sci USA* 82:6517–6521 (1985)).

The original identification of oncofetal fibronectins in pregnancy and tumor tissues was based on the isolation of a novel monoclonal antibody, FDC-6. Matsuura et al., U.S. Pat. No. 4,894,326 issued Jan. 16, 1990. A series of elegant manuscripts by Matsuura, Hakomori, and co-workers have demonstrated that FDC-6 binds to a specific O-linked N-acetygalactosaminylated hexapeptide epitope within the fibronectin type III connecting segment (IIICS) (Matsuura and Hakomori, *Proc Natl Acad Sci USA* 82:6517–6521 (1985); Matsuura et al., *J Biol Chem* 263: 3314–3322; Matsuura et al. (1988), *J Biol Chem* 264:10472–10476 (1989)). This binding site, which requires both the peptide backbone and the carbohydrate moiety to generate the epitope, is not found in high abundance in normal adult fibronectins. Thus, FDC-6 has been incorporated into a sensitive enzyme linked immunoassay5 for the clinical detection of cervicovaginal oncofetal fibronectin.

Detection of oncofetal fibronectin that is abnormally released into the cervix and vagina prior to 37 weeks of gestation has helped identify patients at high risk for preterm labor and delivery (Lockwood et al., *N Engl J Med* 325:669–74 (1991); Morrison et al., *Am J Obstet Gynecol* 168:538–542 (1993); Nageotte et al., *Am J Obstet Gynecol* 166:274 (1992) Lockwood et al., *Am J Obstet Gynecol* 169: 798–804 (1993); Creasy, *Am J Obstet Gynecol* 168:1223–30 (1993)).

It was found, however, that FDC-6 was not suitable for all diagnostic assays because FDC-6 was found to bind to 1–4% of circulating human plasma fibronectin from nonpregnant individuals. As a result, some diagnostic procedures were found to be hindered by false positives. This has been especially true with sensitive diagnostic assays of cervicovaginal FDC-6 reactive fibronectin perhaps due, in part, to overt or occult bleeding and the presence of plasma fibronectin.

Accordingly, novel antibodies for enhancing the specificity of oncofetal fibronectin diagnostic assays are greatly desired.

SUMMARY OF THE INVENTION

In accordance with the present invention are provided immunologic binding partners defined by specifically binding with the carboxy-terminal region of oncofetal fibronectin released by cathepsin D digestion but not with normal adult fibronectin or blood plasma fibronectin. Hybridomas capable of producing said immunologic binding partners are also provided.

Said immunologic binding partners are reactive to oncofetal fibronectin. Accordingly, such immunologic binding partners are useful for the detection of oncofetal fibronectin in biological samples and for the detection and treatment of oncogenesis and reproductive abnormalities related to or indicated by the presence of oncofetal fibronectin.

BRIEF DESCRIPTION OF THE DRAWINGS

FIG. 1.

FIG. 2. Monoclonal antibody X18A4 does not compete with FDC-6 for binding to oncofetal fibronectin.

FIG. 3. Comparative immunocytochemical analysis with antibodies X18A4 (FIGS. 3A, 3C, 3E, 3G) and FDC-6 (FIGS. 3B, 3D, 3F, 3H). FIGS. 3A and 3B: Immunostaining of the placental-decidual junction (white arrows) demonstrated prominent extracellular staining surrounding junctional anchoring trophoblasts (J), with negative placental villous (V) staining. 20X magnification. FIGS. 3C and 3D: Prominent fibrillar staining (F) surrounding tumor nests (T) within parallel sections of a metastatic peritoneal implant of ovarian adenocarcinoma. 20X magnification.

FIG. 6. Glycosidase digestion of oncofetal fibronectin. FIGS. 6A and 6B: Oncofetal fibronectin (5 µg) was treated enzymatically with neuraminidase alone (lanes a,e), serial digestions with neuraminidase and endo-a-N-acetylgalactosaminidase (O-Glycanase) (lanes b,f), O-glycanase alone (lanes c, g), or no enzyme control (lanes d,h). In FIG. 6A, X18A4 binding to de-O-glycosylated oncofetal fibronectin (lane b) was similar to the control (lane d), whereas in FIG. 6B, FDC-6 binding to de-O-glycosylated oncofetal fibronectin (lane f) was significantly reduced compared to the control (lane h). FIG. 6C: X18A4 binding to oncofetal fibronectin was not affected by de-glycosylation with N-glycanase (lane i: 1.0 unit/ml; lane j: 5.0 units/ml; lane k: 10 units/ml) when compared to the no enzyme control (lane 1). FDC-6 yielded an identical binding pattern (not shown). Slight shifts in electrophoretic mobility on immunoblot indicate the effectiveness of the de-glycosylation reactions.

FIG. 7. FIG. 7A FDC-6 binds quantitatively to increasing amounts (2 to 20 µg) of purified human plasma fibronectin. FIG. 7B In a parallel immunoblot, X18A4 has no detectable binding to plasma fibronectin.

DESCRIPTION OF PREFERRED EMBODIMENTS

The murine monoclonal antibodies X18A4, X20C4 and X8E3 were established as described below following immunization with fibronectin and immunosuppression with cyclophosphamide. The hybridomas ATCC# HB11587, ATCC# HB11588 and ATCC# HB11589 were selected by positive reactivity of their antibodies (X18A4, X8E3, X20C4 respectively) with oncofetal fibronectin and by negative reactivity with blood plasma fibronectin as shown in FIG. 1. These antibodies are believed to have very similar or identical epitopes based upon competitive binding assays.

This common binding epitope is unique to antibodies of the present invention including X18A4, X20C4 and X8E3. Antibodies of the present invention have a different binding epitope than FDC-6 as evidenced by the fact that X18A4 does not compete with FDC-6 for binding to oncofetal fibronectin. Accordingly, FDC-6 and antibodies of the present invention including X18A4, X20C4 and X8E3 may be used compatibly in, for example, sandwich assays, thereby providing methods of enhancing the specificity of diagnostic procedures especially in instances wherein blood or plasma may be present.

Figure 4:
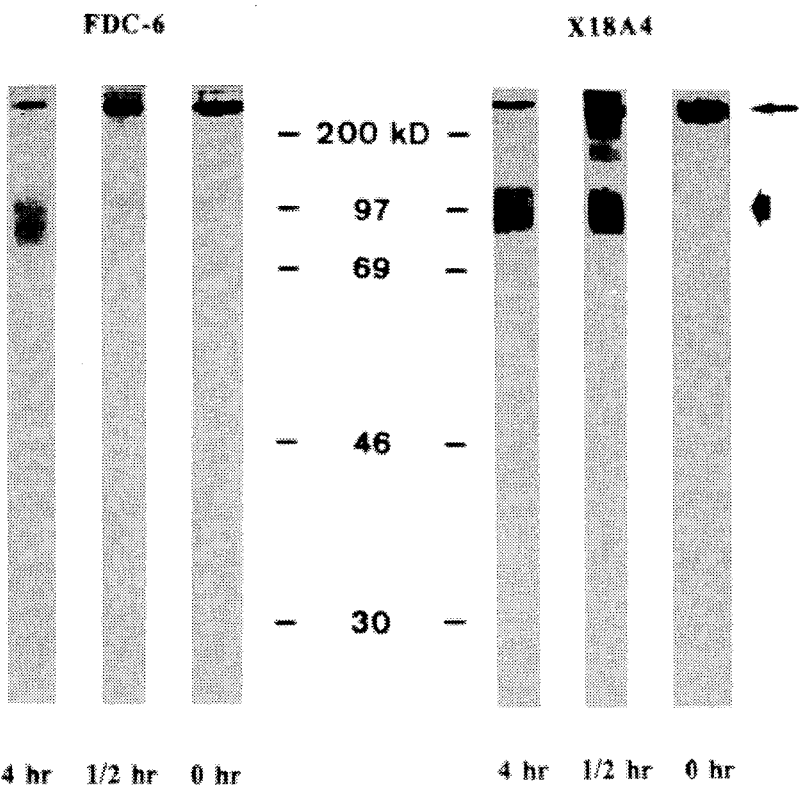
FIG. 4. Cathepsin D digestion of purified hepG2 cell oncofetal fibronectin (10 µg) demonstrated a similar pattern of digestion fragments with FDC-6 or X18A4. After 4 hours of digestion, both antibodies reacted with a doublet of 90 and 110 kD (arrow).

As can be seen in FIG. 4, antibodies of the present invention such as X18A4 react with a doublet of 90 and 110 kD fragments generated by cathepsin D digestion. These fragments correspond to the carboxy terminal of oncofetal fibronectin generated by cathepsin D digestion of the protein. This fragment includes the IIICS region of oncofetal fibronectin. Matsuura and Hakomori, *Proc. Natl. Acad. Sci. USA* 82:6517–6521 (1985).

Figure 5:
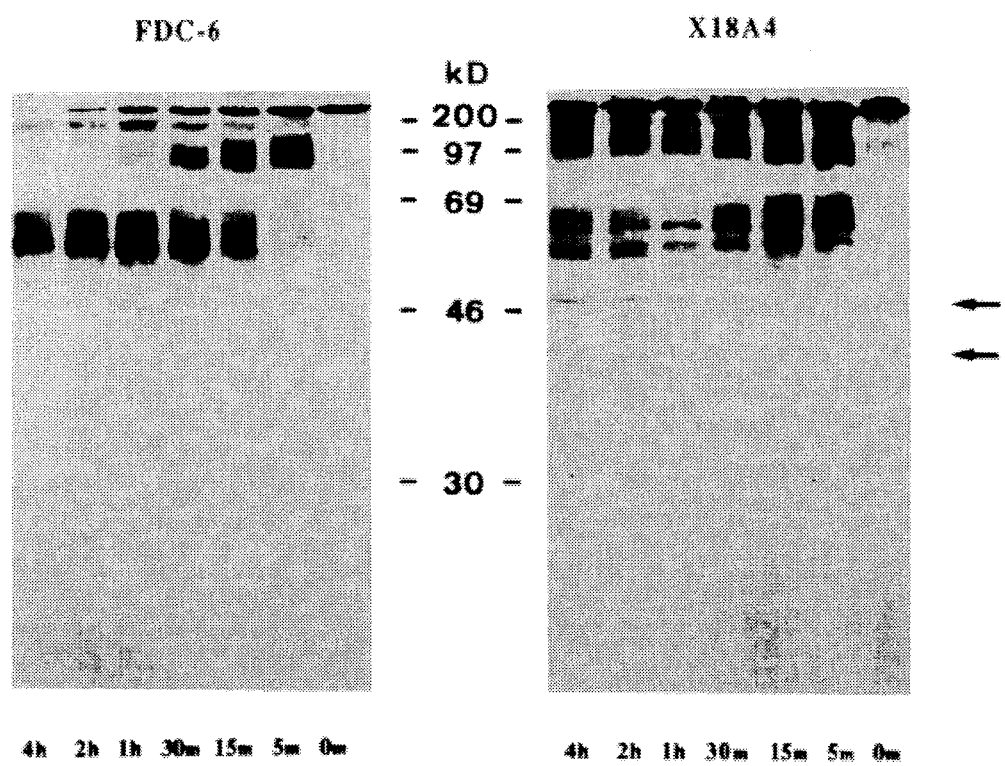
FIG. 5. Trypsin digestion of hep G2 cell oncofetal fibronectin over a 4 hour time yielded multiple bands in the 55 to 65 kD size range reactive with both FDC-6 and X18A4. Two smaller 48 and 40 kD fragments (arrows) bind to X18A4, but not FDC-6.

As shown in FIG. 5, trypsin digestion of oncofetal fibronectin yielded multiple bands in the 55 to 65 kD size range which were reactive to both X18A4 and FDC-6. These bands correspond closely to the different lengths of IIICS peptide backbone represented in the tryptic fragments. In addition, two smaller bands at 48 and 40 kD are recognized only by X18A4.

FIG. 6 shows that unlike FDC-6, X18A4 binding of oncofetal fibronectin is not affected by de-glycosylation of the protein. Thus, X18A4 does not require a combined peptide-carbohydrate moiety for recognition.

Tissue studies showed specific staining of the fibronectin matrix of the placental-decidual junction, but not fibronectin of the villous mesenchymal core or fetal vessel walls. The dense fibronectin matrix of a metastatic implant derived from an epithelial ovarian malignancy was strikingly positive as were less prominent and delicate fibronectin fibrils interspersed within some tumor nests.

Tissue studies suggest that switching from oncofetal fibronectin synthesis to normal fibronectin synthesis is associated with human ontogenesis and that the reverse process is associated with oncogenesis. Accordingly, the structure defined by the antibodies X18A4, X20C4 and X8E3 expressed in oncofetal fibronectin is a useful marker of cancer. As used herein antibody may refer to antibodies as well as other immunologic binding partners such as antigen-binding fragments, chimaeras, etc. The antibodies X18A4, X20C4 and X8E3 and other immunological binding partners directed against this oncofetal fibronectin structure are of practical value in diagnostic tests and in monitoring and implementing various conditions associated with oncofetal fibronectin such as hyperproliferation of cells such as are present in cancer or ectopic pregnancy.

The antibodies of the present invention can be coupled to a radionuclide and introduced into the body of a mammal to image hyperproliferating cells such as cancer cells or abnormal ectopic trophoblast location and/or implement radiotherapy. For example, a radionuclide such as I-123 can be coupled to the antibody X18A4 using standard methodologies, such as those employing the Bolton-Hunter reagent.

The radiolabeled antibody can be admixed in a suitable carrier solution and introduced, e.g., intravenously, into the body of a mammal. The body can thereafter be scanned with a scintillation detector such as a gamma camera to localize the hyperproliferating cells of tumor tissues such as metastases or abnormal ectopic pregnancy trophoblasts bearing oncofetal fibronectin reactive with the radiolabeled antibody.

Antibodies of the present invention are also suitable for implementing cancer or ectopic pregnancy immunological therapy. The antibody can be coupled to an anti-tumor agent such as a radionuclide or an anti-tumor drug, such as mitomycin or methotrexate, and introduced into the body of an adult mammal in order to differentially deliver the radionuclide or drug to hyperproliferating cells bearing oncofetal fibronectin.

The antibodies of the present invention can also be coupled to a detectable marker for immunohistological detection of cells that express oncofetal fibronectin such as hyperproliferating cells that contain oncofetal fibronectin. For example, antibodies of the present invention can be coupled to a radionuclide and used to detect oncofetal fibronectin in an in vitro sample such as blood or tissue samples.

Antibodies of the present invention and other immunological binding partners directed against oncofetal fibronectin structure, preferably detectably labeled, are also of practical value in diagnostic tests and in the monitoring of human reproductive disorders. Such diagnostic tests comprise contacting a biological sample with one or more immunologic binding partners of the present invention and detecting reacted immunologic binding partners after unreacted immunologic binding partners have been removed. Biological samples which may be used in methods of the present invention include, but are not limited to blood, tissue, cells such as fetal cells, trophoblast cells, and tumor cells, amniotic fluid, cervicouterine aspirates, cyst fluids, organ transudates such as transudates from the breast or ovary, ascites, pleural effusions, cerebrospinal fluid, joint aspirates, saliva, urine, semen, salivary gland secretions, vaginal secretions, lung secretions, and gastrointestinal tract secretions.

Since oncofetal fibronectin is specifically produced by implanting and anchoring trophoblast at the chorion-uterine junction, active production of oncofetal fibronectin can provide an early marker for normal trophoblastic implantation. Thus, in some methods of the present invention, immunologic binding partners of the present invention which react with oncofetal fibronectin can provide early detection of implantation which may be especially important for patients undergoing assisted reproductive technologies, for diagnosis of pregnancy in an extra-uterine location such as in the tube, ovary, cervix or abdominal cavity (ectopic pregnancy) and for diagnosis of metastatic gestational trophoblastic disease.

The receptivity of endometrium to implantation can also be detected with assays in which immunologic binding partners of the present invention are employed. In accordance with such methods, the endometrium may be tested for the presence of oncofetal fibronectin such as by immunoassay of an endometrium tissue biopsy or reproductive fluids such as cervicouterine aspirates and vaginal secretions using detectably labeled immunologic binding partners of the present invention. Increased concentrations of oncofetal fibronectin as indicated by bound immunologic binding partner, as compared to an infertile individual, is indicative of greater receptivity of the endometrium to implantation.

Because it has been found that there is an increased serum levels of cellular and plasma fibronectin in patients predisposed to pre-eclampsia or eclampsia due to abnormal trophoblast-uterine or aberrant trophoblast-endothelial cell interactions, immunologic binding partners of the present invention may be used in, for example, an immunoassay, for detection of oncofetal fibronectin during the second and third trimester of pregnancy the results of which are indicative of risk for pre-eclampsia or eclampsia.

Immunologic binding partners of the present invention may also be used in immunoassays for the detection of oncofetal fibronectin levels indicative of abnormal trophoblast-uterine interactions involved in placental abruption.

Furthermore, immunologic binding partners of the present invention may be used in immunoassays to detect oncofetal fibronectin in blood samples. This can be useful for example, to detect the release of amniotic fluid components into the maternal bloodstream which may lead to cardiopulmonary collapse. Antibodies of the present invention which can specifically recognize oncofetal fibronectin present in the maternal bloodstream may also be used to isolate and enrich trophoblast cells circulating in the maternal bloodstream. Such trophoblast cells, once isolated, could be used for analysis of chromosomal and genetic abnormalities of fetal DNA. For example, maternal cells from the buffy coat can be cultured for 24 for 48 hours, tagged with fluorescent X18A4, and trophoblasts separated via fluorescent activated cell sorting (FACS). These separated trophoblasts could be used for cytogenetic, in situ hybridization and PCR analyses.

Immunologic binding partners of the present invention may also be useful in methods of contraception whereby an amount of immunologic binding partner sufficient to decrease the amount of free oncofetal fibronectin in a mammal is administered to the reproductive tract of said mammal, thereby decreasing the probability that implantation will be successful. Said immunologic binding partner may be administered to the reproductive tract of a female mammal. For example, said immunologic binding partner could be applied to the local environment of the uterus through a gel, a suppository, slow release sponge, or directly with a solution vehicle to decrease the amount of oncofetal fibronectin in the reproductive tract available for implantation.

Detectable markers can be selected from among fluorophores, enzymes, chromophors, coenzymes, chemiluminscent materials, enzyme inhibitors, paramagnetic metals such as gadolinium, and radionuclides that are known in the art. Biological samples can be contacted with immunologic binding partner-marker conjugate, and any detectable marker that becomes isolated on the sample can be detected by standard methods after unreacted antibody is removed.

The X18A4, X20C4 and X8E3 antibodies as well as other immunologic binding partners raised against the oncofetal structure can be packaged in kits useful for assaying the presence of oncofetal fibronectin, or for delivering therapeutic agents to the immediate vicinity of cells that express oncofetal fibronectin.

The representative hybridomas ATCC# HB11587, ATCC# HB11588 and ATCC# HB11589 that produced antibodies designated X18A4, X8E3 and X20C4, respectively, were deposited on Mar. 17, 1994 at the American Type Culture Collection, 12301 Parklawn Drive, Rockville, Md., 20852.

The following examples are illustrative and are not meant to be limiting of the present invention.

EXAMPLES

Example 1

Cytotrophoblast culture and oncofetal fibronectin isolation.

Human cytotrophoblasts were purified from the placentae of uncomplicated term pregnancies immediately after delivery by serial trypsin-DNase digestions and Percoll gradient centrifugation, as previously described by Kliman et al (Kliman et al, *Endocrinology* 118:1567–1582 (1986)). Yields of viable mononuclear cytotrophoblasts ranged from 60 to 100×10$^6$ cells per 30 grams of starting placental tissue. Cytotrophoblasts were cultured in Dulbecco's Modified Eagles' Medium (DMEM) containing 25 millimolar glucose and 25 millimolar HEPES, supplemented with 4 millimolar glutamine and 50 µg/ml gentamicin. The DMEM also contained 10% newborn human cord sera as a maximal stimulator of oncofetal fibronectin synthesis in vitro (Feinberg and Kliman, *Troph Res* 7:167–179 (1993)). After 36 to 40 hours in serum-containing media, the cells were washed thoroughly with serum free DMEM, and cultured for an additional 36 to 50 hours in serum free DMEM. Despite the lack of serum at this stage of the culture, the cells continued to synthesize and secrete abundant FDC-6 reactive fibronectin, with media concentrations of 10 to 15 µg/ml. Serum-free conditioned media from human HepG2 hepatoma cells and residual amniotic fluid following therapeutic amniocentesis for hydramnios were also used as a sources of oncofetal fibronectin. Fibronectin from conditioned media or amniotic fluid was purified by gelatin-Sepharose 4B chromatography (Pharmacia) (Engvall and Ruoslahti, *Int J Cancer* 20:1–5 (1977)).

Example 2

Preparation of hybridomas and antibodies

The identification of specific anti-oncofetal fibronectin antibodies utilized an approach incorporating in vivo suppression of the immune response to plasma fibronectin, as well as an in vitro boost of splenic lymphocytes with trophoblast oncofetal fibronectin. Six week old Balb/c mice were immunized intraperitoneally (IP) with 20 µg plasma fibronectin and cyclophosphamide was administered (100 mg/kg of body weight) two days later; Matthew and Sandrock, Jr., *J. Immunol. Meth.* 100:73–82 (1987); to suppress the immune response to plasma fibronectin. An alternating series of IP and subcutaneous injections with oncofetal fibronectin was initiated one week after immunosuppression with cyclophosphamide. After four doses of oncofetal fibronectin (15 µg each, approximately 2 weeks apart), one mouse was sacrificed, the spleen dissected, splenocytes were perfused out, erythrocytes were lysed by suspension in 0.14M ice cold $NH_4Cl$ for 8 minutes and splenocytes were incubated for 2 days in 0.1 µg/ml oncofetal fibronectin in hybridoma medium (HM; 72% DMEM, 4.5 g/l glucose, 8% NCTC135, 20% FCS, with 4 mM L-glutamine, 0.15 mg.ml oxaloacetate, 0.05 mg/ml pyruvate, 0.2IU/ml insulin, 100 U/ml penicillin, 100 U/ml streptomycin) supplemented with 20% Origen growth supplement (IGen) and 20 U/ml IL-2. The in vitro stimulated lymphocytes were fused with Sp2/OAg14 myeloma cells according to the procedure of Lane et al., *Methods in Enzymology* 121:183–192 (1986). Hybridomas were cultured in HM supplemented with 10% P388 supernatant, 30 µg/ml carboxyethyl GABA, 0.1 mM hypoxanthine and 6 µM azaserine, fed at one week after fusion, and yellow supernatants from wells containing hybridomas were harvested and tested for reactivity to plasma and oncofetal fibronectin. Hybridomas from positive wells were cloned by limited dilution in HM supplemented with 10% Origen or P388 supernatant, and positive subclones were identified, cultured and frozen. Positive hybridomas HB11587 (X18A4); HB11588 (X8E3); and HB11589 (X20C4) were deposited on Mar. 17, 1994 at the American Type Culture Collection, 12301 Parklawn Drive, Rockville, Md., 20852.

Example 3

Immunoassays

The initial comparative immunoassay screen with hybridoma supernatants utilized microtiter plates precoated with amniotic fluid oncofetal fibronectin, trophoblast oncofetal fibronectin, or human plasma fibronectin. Immunodetection of antibody binding was performed with a biotinylated anti-mouse secondary antibody, avidin, and biotinylated horseradish peroxidase, according to the manufacturer's instructions (ABC Vectastain, Vector Labs, Burlingame, Calif.). Hybridoma supernatants which demonstrated selective binding to oncofetal fibronectins were further analyzed by comparative Western immunoblots as described in Example 4.

Of the 1337 hybridoma clones screened, 13 (10%) demonstrated similar binding activities to plasma or oncofetal fibronectin. Of these, three clonal supernatants X18A4, X20C4, and X8E3 exhibited specific binding to amniotic fluid and trophoblast oncofetal fibronectin on enzyme-linked immunoabsorbent assay, but not plasma fibronectin. FIG. 1 demonstrates the specific binding activity of X18A4 to oncofetal fibronectin by Western immunoblot, under both reducing and non-reducing conditions. Clone X15H1 is an example of an anti-fibronectin clone identified in the screening which binds equally to plasma and oncofetal fibronectin. Of the three specific clones identified, X18A4 exhibited at least 10-fold stronger binding activity for oncofetal fibronectin than X20C4 or X8E3. For immunoassays, X18A4 maintained high sensitivity at antibody concentrations of 0.5 to 2 µg/ml, whereas X20C4 and X8E3 typically required 20 µg/ml of antibody or higher. Antibody X18A4 is an IgM molecule, as determined by isotypic ELISAs and Western blots utilizing subclass specific anti-mouse mu antibodies. (Boehringer-Mannheim and Vector Labs), whereas X20C4 and X8E3 are IgG antibodies.

Example 4

Western Immunoblots

For Western immunoblot analyses, samples were electrophoresed in 6% SDS-polyacrylamide gels, under reducing or non-reducing conditions. Gels were electrotransferred to nitrocellulose (Schleicher and Schull, Keene, N.H.) overnight. For blots incubated with antibodies FDC-6 or X18A4, antibody concentrations of 1 to 3 µg/ml were utilized. Immunodetection was carried out with ABC Vectastain (Vector Labs) and the insoluble chromagen 3,3'-diaminobenzidine (Sigma).

Figure 2A:
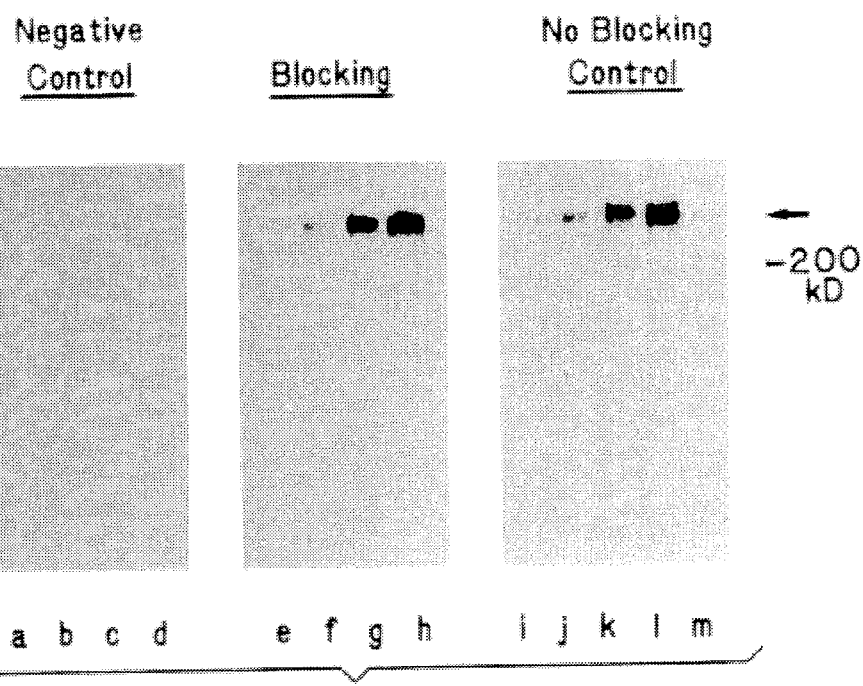
FIG. 2A Blots were pre-incubated with X18A4 (lanes a–h) or antibody diluent (lanes i–m), then reacted with diluent (lanes a–d) or FDC-6 (lanes e–m). Blots in FIG. 2A were then developed with a biotinylated anti-gamma chain specific antibody to detect FDC-6, but not X18A4 binding. Pre-incubation with X18A4 had no demonstrable blocking effect on FDC-6 binding.
Figure 2B:
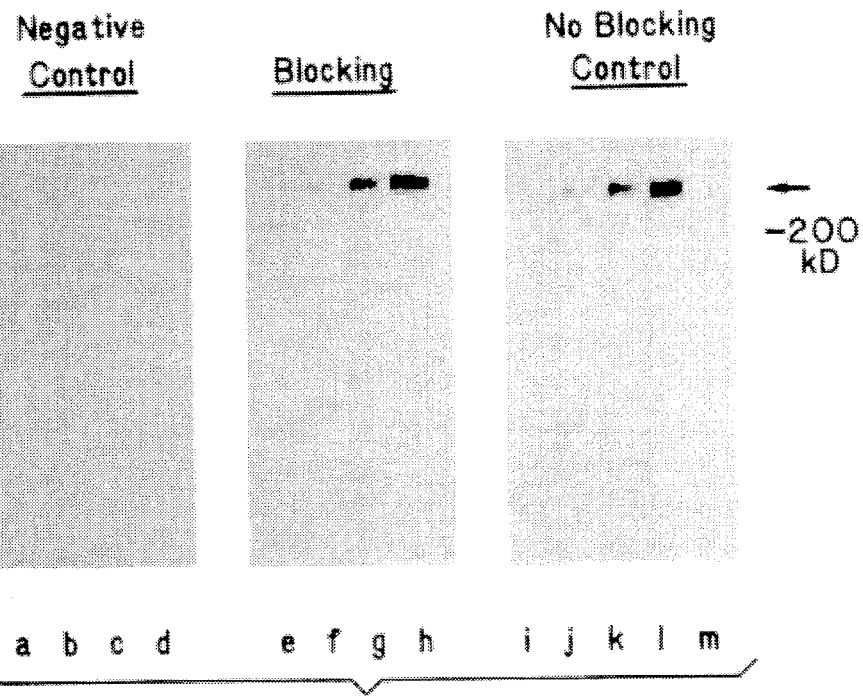
FIG. 2B Blots were pre-incubated with FDC-6 (lanes a–h) or diluent (lanes i–m), then reacted with diluent (lanes a–d) or X18A4 (lanes e–m). Blots in FIG. 2B were then developed with a biotinylated anti-mu chain specific antibody to detect X18A4, but not FDC-6. Pre-incubation with FDC-6 does not block or diminish X18A4 binding to oncofetal fibronectin. Samples loaded: oncofetal fibronectin 50 ng (lanes a,e,i); 100 ng (lanes b, f, j); 250 ng (lanes c, g, k); 500 ng (lanes d, h, l); plasma fibronectin 500 ng (lane m).

In order to perform competition studies with Western immunoblots it was useful to take advantage of the fact that X18A4 and FDC-6 are different classes of immunoglobulin. As shown in FIGS. 2A–2C, pre-incubation of the immunoblots with a 10-fold higher concentration of X18A4 did not inhibit FDC-6 binding. Conversely, FDC-6 pre-incubation did not block X18A4 binding (FIGS. 2B–2D). This lack of competitive inhibition suggests that X18A4 and FDC-6 bind to distinct epitopes within the oncofetal fibronectin molecule. Interestingly, X18A4 pre-incubation significantly blocks both X20C4 and X8E3 binding (not shown), suggesting that the three clones isolated by the comparative screen react with a very similar or identical non-FDC-6 oncofetal fibronectin epitope.

Example 5

Double-monoclonal FDC-6 and X18A4 immunoassay.

Figure 8:
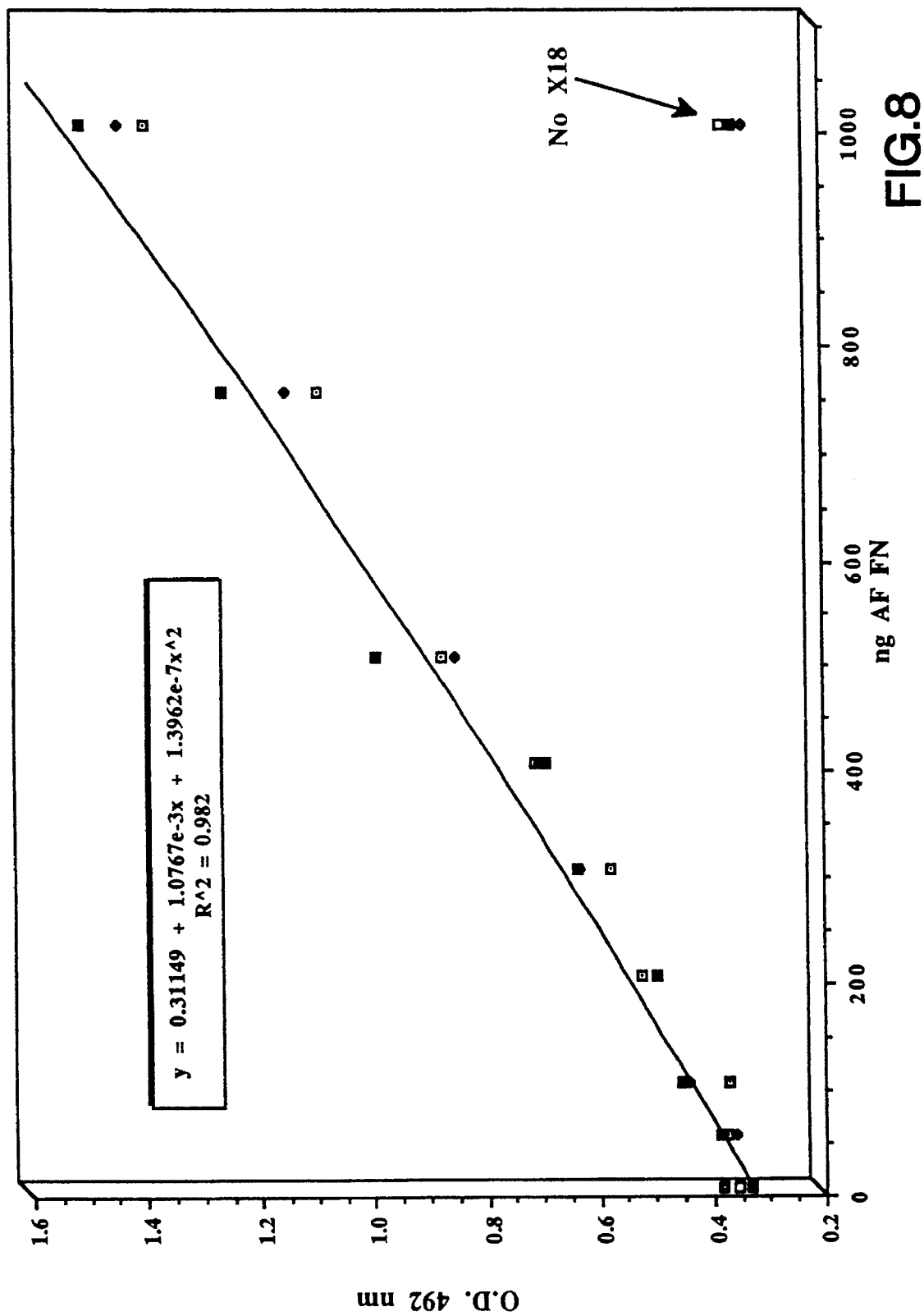
FIG. 8. In this double monoclonal "sandwich"-type immunoabsorbent assay, X18A4 reacted quantitatively with increasing amounts of purified amniotic fluid oncofetal fibronectin, but had no binding activity to plasma fibronectin. For this assay, commercially available microtiter plates precoated with FDC-6 were utilized.

Enzyme-linked immunoabsorbent sandwich assays were carried out with 96-well plates pre-coated with an IgG fraction of murine ascites containing FDC-6, kindly provided by Adeza Biomedical, Sunnyvale, Calif. Known standards of oncofetal fibronectin were used as the antigen. Immunodetection was performed with X18A4 and a highly specific biotinylated anti-mouse mu chain antibody, utilizing the Vectastain protocol. A best fit curve was created with CricketGraph 1.3.2 for the Macintosh (Computer Associates, Garden City, N.Y.) with r2 values greater than 0.98. X18A4 was substituted for the polyclonal anti-fibronectin antibody in commercially obtained 96 well plates pre-coated with FDC-6. As shown in FIG. 8, a standard curve with increasing quantities of oncofetal fibronectin was generated, whereas plasma fibronectin had no activity in this assay. Identical results were obtained when the position of the antibodies was reversed, i.e. when X18A4 was used as the "capture" antibody on the bottom of the sandwich, and FDC-6 was employed as the "reporter" antibody on top. The ability to use X18A4 and FDC-6 together in this type of sandwich immunoassay provides further evidence that the two monoclonal antibodies bind to distinct epitopes within oncofetal fibronectin.

Example 6

Immunocytochemistry.

Five micrometer thick sections of frozen placental or metastatic ovarian carcinoma tissue were placed on glass slides (Probe-On, Fisher Scientific), fixed with cold acetone, and stored in a −200 freezer until use. SPA-26 cells, a first trimester immortalized trophoblast cell line (kind gift of Dr. Janice Chou, National Institute of Health)(Chou J., *Proc Natl Acad Sci USA* 75:1854–1858 (1978)) were cultured on glass coverslips and fixed with formalin. Primary antibodies FDC-6 (American Type Culture Collection, Bethesda, Md.) and X18A4 were diluted from hybridoma supernatants and were used at antibody concentrations of 1 to 3 μg/ml. Control slides, which yielded negative staining, were incubated with undiluted ATCC P3X63Ag8 mouse myeloma cell line supernatant. Immunodetection with Vectastain ABC and counterstaining with hematoxylin were carried out as recommended by the manufacturer (Vector Labs).

Figure 3F:
FIGS. 3E and 3F: Delicate fibrillar staining within certain tumor nests revealed very thin fibronectin fibrils (arrowheads), along with more developed, thicker areas of fibronectin (arrows). 40X magnification.
Figure 3H:
FIGS. 3G and 3H: SPA-26 cells, a first trimester non-malignant trophoblast cell line, produces and deposits abundant X18A4 and FDC-6 reactive extracellular fibronectin fibrils. 40X magnification.
Figure 3E:
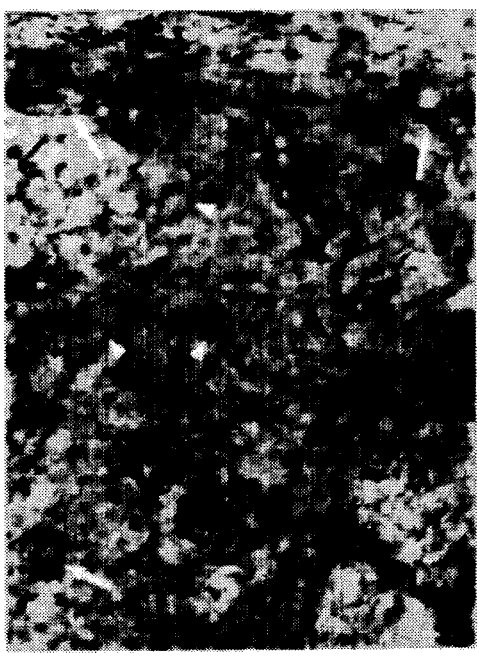
Figure 3G:

Immunohistochemical analysis of the placental-decidual junction (FIGS. 3A and 3B) revealed prominent extracellular staining with both antibodies. As previously described for FDC-6,1,2 X18A4 did not stain fibronectin within the villous mesenchymal core or in fetal blood vessel walls. The two antibodies yielded an identical staining pattern within parallel sections from a metastatic implant of ovarian adenocarcinoma, demonstrating strong staining around some epithelial tumor nests (FIGS. 3C and 3D) and fine fibrillar staining within others (FIGS. 3E and 3F). SPA-26 cells, a first trimester trophoblast line immortalized by SV40 transfection, (Chou J., *Proc Natl Acad Sci USA* 75:1854–1858 (1978)) also produced abundant FDC-6 and X18A4 reactive extracellular fibronectin fibrils (FIGS. 3G and 3H).

Example 7

Protease and de-glycosylation reactions.

Purified hepG2 hepatoma oncofetal fibronectin was digested with 1.25 U/ml cathepsin D (Sigma) or 2.5 U/ml trypsin (Sigma) in a buffer containing 50 mM TRIS-HCl pH 9.0, 2M urea and 20 μM dithiothreitol. Hepatoma oncofetal fibronectin was also treated with 1–10 units/ml glycopeptidase F (Sigma)., which releases N-linked carbohydrate moieties, in a buffer containing 0.25M Na phosphate, pH 8.6. De-O-glycosylation was carried out by pre-incubation with 1.0 units/ml sialidase (neuraminidase) (Genzyme Corp.., Boston, Mass.) for one hour, followed by addition of 30 milliunits/ml of endo-a-N-acetylgalactosaminidase (O-Glycanase, Genzyme Corp., Boston, Mass.) in a buffer containing 50 mM sodium acetate and 1 mM CaCl2, pH 6.0 at 37° overnight. Control samples for all enzymatic reactions were incubated in the appropriate buffers in the absence of enzyme. All digestion products were analyzed by Western immunoblots.

As shown in FIG. 4, X18A4 reacted with a broad doublet of approximately 90 and 110 kD generated by cathepsin D digestion, similar to FDC-6 reactive fragments analyzed in parallel. These fragments correspond to the carboxy side of the fibronectin monomer, and include the IIICS region (Matsuura and Hakomori, Proc *Natl Acad Sci USA* 82:6517–6521 (1985)). Similarly, trypsin digestion yielded multiple bands in the 55 to 65 kD size range reactive with both FDC-6 and X18A4 (FIG. 5). As described by Matsuura and Hakomori, the size diversity of these bands corresponds closely to the different lengths of IIICS peptide backbone represented in the tryptic fragments.4 Interestingly, two smaller bands of molecular weights 48 and 40 kD exhibit X18A4 binding, but not FDC-6 reactivity. Thus, X18A4 appears to bind to a non-FDC-6 site near or within the IIICS region.

In order to determine if the X18A4 epitope is associated with O-glycosylation, oncofetal fibronectin was treated enzymatically with neuraminidase and endo-a-N-acetylgalactosaminidase (O-Glycanase). While FDC-6 binding was sensitive to enzymatic de-O-glycosylation (FIG. 6B), X18A4 binding was not affected (FIG. 6B). Enzymatic de-glycosylation of N-linked carbohydrate residues also had no effect on X18A4 binding (FIG. 6C). Therefore, the X18A4 epitope appears to differ significantly from the FDC-6 binding site by not requiring O-linked N-acetylgalactosaminylation at a serine or threonine residue.

Example 8

Comparative binding to human plasma fibronectin

Western Immunoblots, performed as described in Example 3, were used to compare binding of FDC-6 and X18A4 to human plasma fibronectin. FIG. 7 shows quantitative binding of FDC-6 to increasing amounts of human plasma fibronectin (2 to 20 μg). X18A4 has no detectable binding to plasma fibronectin.

What is claimed is:

1. An immunologic binding partner produced by hybridoma cell line ATCC #HB11587, said immunologic binding partner having specific binding affinity for the carboxy-terminal region of oncofetal fibronectin released by cathepsin D digestion but not with normal adult fibronectin or blood plasma fibronectin.

2. An immunologic binding partner produced by hybridoma cell line ATCC #HB11588, said immunologic binding partner having specific binding affinity for the carboxy-terminal region of oncofetal fibronectin released by cathepsin D digestion but not with normal adult fibronectin or blood plasma fibronectin.

3. An immunologic binding partner produced by hybridoma cell line ATCC #HB11589, said immunologic binding partner having specific binding affinity for the carboxy-terminal region of oncofetal fibronectin released by cathepsin D digestion but not with normal adult fibronectin or blood plasma fibronectin.

4. Hybridoma cell line ATCC HB 11587.

5. Hybridoma cell line ATCC HB 11588.

6. Hybridoma cell line ATCC HB 11589.

* * * * *

UNITED STATES PATENT AND TRADEMARK OFFICE
CERTIFICATE OF CORRECTION

Figure 1A:
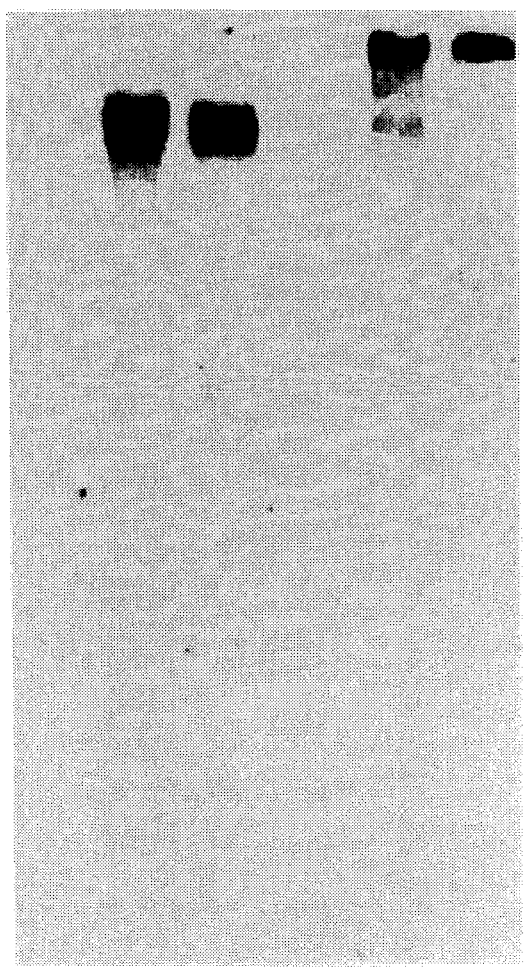
FIG. 1A Monoclonal antibody X18A4 does not bind to purified human plasma fibronectin (lanes a, d), but reacts strongly with 500 ng of purified amniotic fluid fibronectin (lanes b, e) and 500 ng of purified trophoblast fibronectin (lanes c, f). Specificity of binding is apparent whether samples are electrophoresed in reducing (lane a–c) or non-reducing (lanes d–f) buffers.
Figure 1B:
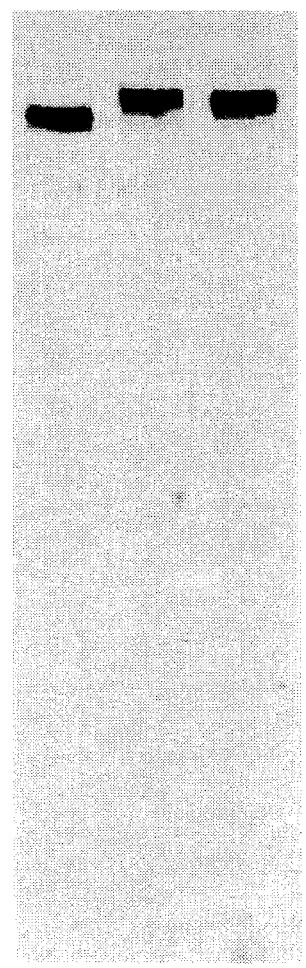
FIG. 1B Monoclonal antibody X15H1, typical of the non-specific anti-trophoblast fibronectin antibodies, binds equally well to plasma fibronectin, amniotic fluid fibronectin, and oncofetal fibronectin (lanes g–i).

PATENT NO. : 5,523,229
DATED : June 4, 1996
INVENTOR(S) : Ronald F. Feinberg and Harvey J. Kliman It is certified that error appears in the above-indentified patent and that said Letters Patent is hereby corrected as shown below:

At Column 3, line 48, delete "FIG.1" and insert -- Figures 1A and 1B -- therefor.

At Column 4, line 10, delete "FIG.6" and insert -- Figures 6A, 6B and 6C -- therefor.

At Column 8, line 6, delete "FIG.1" and insert -- Figures 1A and 1B -- therefor.

At Column 10, line 33, delete "FIG.7" and insert -- Figures 7A and 7B -- therefor.

Signed and Sealed this

Eighth Day of October, 1996

BRUCE LEHMAN

*Attest:*

*Attesting Officer*     *Commissioner of Patents and Trademarks*